United States Patent [19]

Hou

[11] Patent Number: 5,852,196

[45] Date of Patent: Dec. 22, 1998

[54] 12,13,17-TRIHYDROXY-9(Z)-OCTADEOENOIC ACID AND DERIVATIVES AND MICROBIAL ISOLATE FOR PRODUCTION OF THE ACID

[75] Inventor: Ching T. Hou, Peoria, Ill.

[73] Assignee: The United States of America as represented by the Secretary of the Agriculture, Washington, D.C.

[21] Appl. No.: 814,674

[22] Filed: Mar. 11, 1997

[51] Int. Cl.⁶ .................................................. C07C 229/00
[52] U.S. Cl. ........................ 554/103; 554/108; 554/213; 554/223; 554/225; 554/226; 554/229; 435/134; 435/135; 435/146; 435/232.1; 435/232.7; 435/842

[58] Field of Search ..................................... 584/103, 108, 584/213, 253, 225, 226, 229; 435/134, 135, 146, 252.1, 252.7, 842

*Primary Examiner*—Gary Geist
*Assistant Examiner*—Deborah D. Carr
*Attorney, Agent, or Firm*—M. Howard Silverstein; Curtis P. Ribando; John D. Fado

[57] ABSTRACT

A novel compound, 12,13,17-trihydroxy-9(Z)-octadecenoic acid (THOA) was produced from linoleic acid by microbial transformation at 25% yield. The newly isolated microbial strain catalyzing this transformation was identified as Clavibacter sp. ALA2 (Accession No. NRRL B-21660). THOA and its derivatives have application as antifungal agents.

6 Claims, 1 Drawing Sheet

12,13,17-TRIHYDROXY-9(Z)-OCTADEOENOIC ACID AND DERIVATIVES AND MICROBIAL ISOLATE FOR PRODUCTION OF THE ACID

BACKGROUND OF THE INVENTION

1. Field of the Invention

This invention relates to a novel trihydroxy fatty acid, derivatives thereof, and to a novel microbial isolate for producing the acid.

2. Description of the Prior Art

Microbial conversions of unsaturated fatty acids have been widely exploited. Microbial production of monohydroxy fatty (10-hydroxy stearic) acid was first reported by Wallen et al. The literature reveals that oleic acid is converted to 10-hydroxy- and 10-keto-stearic acids by hydratases in many bacteria and fungi. The hydratases from Flavibacterium sp. DS5 and others are C10- positional specific enzymes. Production of dihydroxy unsaturated fatty acids has also been reported. Oleic acid was converted to 7,10-dihydroxy-8(E)-octadecenoic acid via a 10-hydroxy-8(Z)-octadecenoic acid as intermediate. Microbial oxidation of di-, and poly-unsaturated fatty acids has been reported. Linoleic and linolenic acids were converted to 10-hydroxy-12(Z)-octadecenoic and 10-hydroxy-12(Z),15(Z)-octadecadienoic acid, respectively, by Nocardia and *Flavobacterium*. Dihydroxy-unsaturated fatty acids have also been synthesized from oleic acid by using selenium dioxide as catalyst.

Oxygenated metabolites of unsaturated fatty acids play a variety of important roles in biological systems. Enzymatic conversion of lipid hydroperoxides, products of reactions catalyzed by lipoxygenase, has been reported in many higher plants. Hydroperoxide isomerase converts lipid hydroperoxides to trihydroxy fatty acids. Hydroperoxide isomerase from flaxseed was the first enzyme found that could metabolize lipid hydroperoxides to α- and β- ketols. 8,9,13-Trihydroxy docosanoic acid was produced by yeast as an extracellular lipid. 9,10,13-Trihydroxy-11(E)- and 9,12,13-trihydroxy-10(E)-octadecenoic acids were detected in beer. It has been suggested that these trihydroxy fatty acids are formed from linoleic acid during the process of malting and mashing of barley. Gardner et al. reported the production of diastereomeric 11,12,13-trihydroxy-9(z)-octadecenoic acids and four isomers of 9,12,13(9,10,13)-trihydroxy-10(11)(E)-octadecenoic acids by acid-catalyzed transformation of 13(S)-hydroperoxylinoleic acid. It was also reported that hydroxy and epoxy unsaturated fatty acids present in some rice cultivars acted as antifungal substances and were active against rice blast fungus. It was postulated that these fatty acids were derivatives of linoleic and linolenic acid hydroperoxides. Recently, mixed hydroxy fatty acids were isolated from a variety of rice plant, Sasanishiki, suffering from the rice blast disease and were shown to be active against the fungus. The structures of these fatty acids were identified as 9S,12S,13S-trihydroxy-10-octadecenoic acid and 9S, 12S, 13S-trihydroxy-10,15-octadecadienoic acid. 9,12,13-Trihydroxy-10(E)-octadecenoic acid was also isolated from *Colocasia antiquorum* inoculated with *Ceratocystis fimbriata,* and showed anti-black rot fungal activity. A method has been developed for regio- and stereochemical analyses of trihydroxy unsaturated fatty acids.

SUMMARY OF THE INVENTION

I have now discovered that trihydroxy unsaturated fatty acids can be produced by microbial transformation. In conjunction with this discovery, a novel compound, 12,13,17-trihydroxy-9(Z)-octadecenoic acid (THOA), has been produced from linoleic acid by a new microbial isolate, Clavibacter sp. ALA2.

It is an object of the invention to introduce THOA and certain derivatives thereof as a novel family of organic compounds useful as antifungal agents.

It is also an object of the invention to introduce Clavibacter sp. ALA2 as a novel isolate useful for producing THOA from linoleic acid.

It is another object of the invention to present a method for the isolation and purification of THOA from a culture medium.

Other objects and advantages of the invention will become apparent from the ensuing description.

DEPOSIT OF BIOLOGICAL MATERIAL

Figure 1:
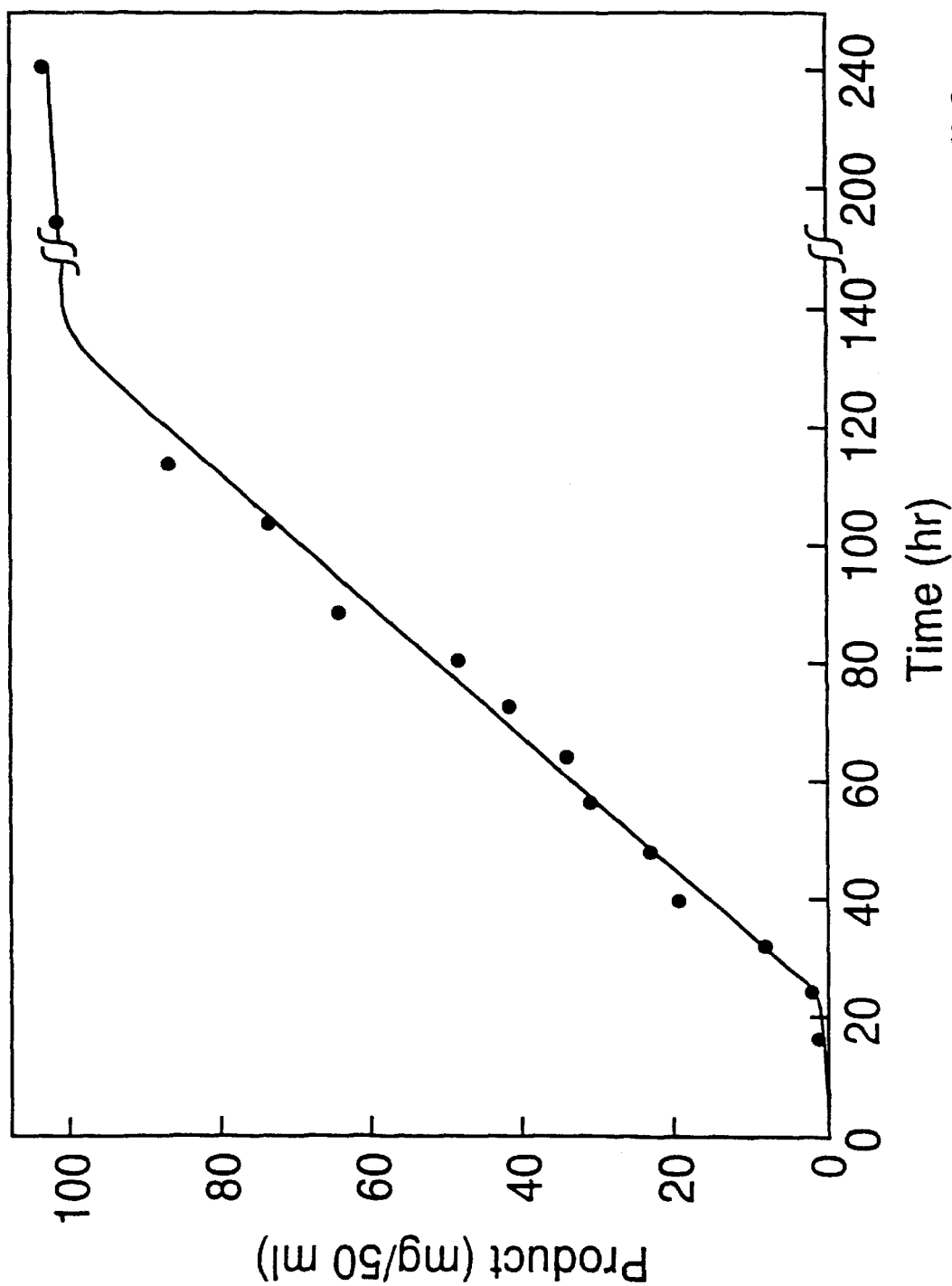
FIG. 1 is the time course of the production of THOA from linoleic acid by Clavibacter sp. ALA2.

Clavibacter sp. strain ALA2 described herein was deposited on Mar. 5, 1997, under the provisions of the Budapest Treaty in the Agricultural Research Culture Collection (NRRL) in Peoria, Ill., and has been assigned Accession No. NRRL B-21660.

DETAILED DESCRIPTION OF THE INVENTION

The novel group of compounds of the invention is represented by the following structural formula:

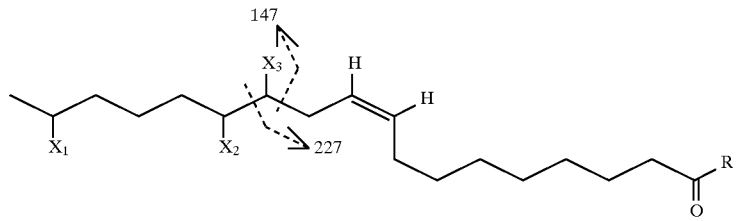

wherein:

R is $-(O)_n-R_1$, n is 0,1, and $R_1$ is H, or a hydrocarbon selected from the group consisting of substituted or unsubstituted alkyl, phenyl, or alkyl phenyl hydrocarbons, wherein the alkyl moiety may be branched or straight chain; and wherein:

$X_1$, $X_2$, and $X_3$ are independently selected from hydroxyl, halogen, or $NR_2R_3$, wherein $R_2$ and $R_3$ are independently selected from the group consisting of hydrogen, substituted or unsubstituted alkyl, phenyl, or alkyl phenyl hydrocarbons, wherein the alkyl moiety may be branched or straight chain.

Of particular interest is the compound THOA and lower, straight chain alkyl esters (1–6 carbons).

As previously stated, THOA can be produced by conversion of linoleic acid or a linoleic acid-containing substrate using Clavibacter sp. strain ALA2. The cultivation may be conducted essentially as described below in the examples. As indicated in Tables II and III, the pH should be maintained between about 6.5 and 8, and the temperature should be maintained between about 25° C. and 40° C. The preferred conditions are pH 6.5 to 7.5 and a temperature within the range of 25° C. to 35° C. Of course it is understood that variations in the medium nutrients and conditions of cultivation may be made as within the skill of person in the art.

The THOA may be isolated by a variety of means, including solvent extraction, liquid chromatography, high performance liquid chromatography, or the like. A 92/8 v/v methylene chloride/methanol is a suitable solvent system for THOA, though the skilled artisan would recognize that other solvent systems would also be operable. The degree of purification would depend upon the prospective end use of the compound, though for most uses it would be desired to isolate the compound in substantially pure form. Derivatives of THOA as encompassed within the scope of the above structural formula are obtainable by conventional reactions of hydroxy and/or carbonyl functional groups as known in the art.

The activity of THOA and its derivatives would be analogous to that characteristic of the trihydroxy unsaturated fatty acids extracted from plants as previously described. Compounds of this class are known to have antifungal, anticancer and other physiological activities. Of particular interest is the use of the compounds of the invention as antifungal agents.

For most applications, the pure or substantially pure compound would be combined with a suitable carrier or vehicle or otherwise incorporated into a formulation intended for application to a target site.

The following examples are presented only to further illustrate the invention and are not intended to limit the scope of the invention which is defined by the claims.

EXAMPLE 1

Microorganisms

Microorganisms from soil and water samples were screened for their ability to modify linoleic acid. Each isolate from a single colony on DISCO TGY agar plates was grown at 30° C. aerobically in a 125-mL Erlenmeyer flask (shaker at 200 rpm) containing 50 mL of medium with the following composition (per liter): dextrose, 10 g; $K_2HPO_4$, 5 g; yeast extract, 5 g; soybean meal, 5 g; $FeSO_4 \cdot 7H_2O$, 0.5 g; $ZnSO_4$, 0.014 g; $MnSO_4 \cdot H_2O$, 0.008 g; and nicotinic acid, 0.01 g. The medium was adjusted to pH 7.0 with dilute phosphoric acid. Cultures were maintained on agar slant with the above mentioned medium except the addition of 3% agar. Microbial isolates were identified by Biolog® automated bacteria and yeast identification system (Microstation, Hayward, Calif.).

Identification of Microorganism

Of the hundreds of water and soil samples screened, only one culture designated ALA2, isolated from a dry soil sample collected from McCalla, Ala., converted linoleic acid to more polar compounds at greater than trace amounts. Strain ALA2 is a Gram (+), nonmotile rod (0.5 $\mu$m×2 $\mu$m). The following 52 of the 96 wells of the Biolog® GN microplate showed positive results: dextrin, glycogen, Tween, N-acetyl-D-glucosamine, D-arabitol, cellobiose, D-galactose, gentiobiose, inositol, α-D-lactose, lactulose, maltose, D-mannitol, D-psicose, D-raffinose, L-rhamnose, D-sorbitol, sucrose, D-trehalose, xylitol, methyl pyruvate, acetic acid, citric acid, formic acid, D-galactonic acid lactone, α-hydroxybutyric acid, γ-hydroxybutyric acid, itaconic acid, α-keto butyric acid, α-keto valeric acid, propionic acid, succinic acid, D-alanine, L-alanine, L-aspartic acid, glycyl-L-aspartic acid, glycyl-L-glutamic acid, hydroxy L-proline, L-phenylalanine, D-serine, L-serine, L-threonine, D,L-carnitine, urocanic acid, inosine, thymidine, phenyl ethylamine, 2-amino ethanol, 2,3-butandiol, glycerol, glucose-1-phosphate and glucose-6-phosphate.

Further identification with the Biolog® automated bacteria identification system showed strain ALA2 belongs to genus Clavibacter, and has a 59% biochemical similarity to the closest species of michiganese. Therefore, strain ALA2 has been assigned as Clavibacter sp. ALA2 and has been deposited in the ARS Culture Collection as NRRL B-21660.

Chemicals

Linoleic and oleic acids were purchased from Nuchek Prep Inc. (Elysian, Minn.). All solvents used were HPLC grade and were obtained from commercial sources. Kieselgel® 60 and thin-layer precoated Kieselgel® $60F_{254}$ plates were obtained from EM Science (Cherry Hill, N.J.).

Bioconversion

Bioconversions were carried out by adding 0.25 mL (0.22 g) linoleic acid to a 24-h-old culture, and the flasks were shaken again at 200 rpm at 30° C. for 2–3 days. At the end of this time, the culture broth was acidified to pH 2 with 6N hydrochloric acid. The culture broth was then extracted with an equal volume of ethyl acetate and then diethyl ether. The solvent was removed from the combined extracts with a rotary evaporator.

Purification of Products

Crude extracts containing reaction products were subjected to high performance liquid chromatography (HPLC) to isolate pure material for further identification. A Dynamax-60A® silica column (25 cm×21.4 mm id., Rainin Instrument Co., Emeryville, Calif.) using methylene chloride/methanol (92/8 v/v) as solvent was used with a DuPont Instruments (Wilmington, Del.) chromatographic pump equipped with a Waters Model 403 refractive index detector (Marlborough, Mass.) and an ISCO Inc. (Lincoln, Neb.) $V^4$ variable wavelength detector. Purity of fractions was analyzed with thin-layer chromatography (TLC) and GC. The main reaction product, purified by HPLC is a colorless, oily liquid. It showed a single spot (Rf=0.14) on TLC and 93% purity by GC.

Analyses of Products

The reaction products were analyzed by TLC and GC as described previously by Hou et al. and Hou et al. Toluene/dioxane/acetic acid (79/14/7, v/v/v) was the TLC solvent system. For GC, the samples were methylated with diazomethane, and then analyzed with a Hewlett Packard 5890 gas chromatograph (Wilmington, Del.) equipped with flame ionization detector, a Supelco SPB-1 capillary column (15 m; id 0.32 mm; 0.25 µm thickness) and a Hewlett Packard 3392A integrater. GC was run isothermally at 210° C. For quantitative analysis, palmitic acid was added as internal standard prior to the solvent extraction. Methyl palmitate was used as a standard to establish a linear relationship between mass and peak area and to calculate the amount of analyte in samples assayed by GC.

Chemical structure of the product was identified through mass spectrometry (MS), nuclear magnetic resonance (NMR) spectroscopy, and Fourier transform infrared (FTIR) measurement. EI and CI mass spectra were obtained with a VG 70-VSE high resolution mass spectrometer. Electron energy and emission current for EI and CI were 70 eV and 130 eV and 100 µA and 200 µA, respectively. Ion source temperature was 200° C., and probe temperature was a gradient from 25°14 175° C. Data acquisition and processing were controlled by the VG OPUS data system running on a VAX station 4000 computer. Proton and $^{13}$C NMR spectra were determined in deuterated chloroform with a Bruker WM-300 spectrometer (Rheins, Tepten, Germany) operating at a frequency of 300 MHZ, respectively. FTIR analysis of both free acid and methyl ester of the product were run in smear on a Mattson infrared Fourier transform CYGNUS 25 spectrometer (Mattson Instruments, Inc., Madison, Wis.).

The CI spectrum of the methyl ester prepared with diazomethane gave a molecular ion of m/z 345. Fragments of 327 (M-18), and 309 (M-2×18) were also seen. The EI spectrum of the methylated product provided more fragments for structural analysis. Ions formed from α-cleavage with respect to the hydroxy-group give characteristic fragmentation patterns that provide sufficient information to determine the position of the hydroxy group. Large fragments corresponding to α-cleavage with ions m/z 227 (25%) and 129 (100%) place hydroxy groups at the C-12 and C-13 positions, and the third hydroxy group at a position between carbons 14 and carbon 18. This was further confirmed by GC/MS of the TMS-derivative of the product which gave large fragments at m/z 299 (18%), 273 (14%) and 171 (100%). These results indicate the product is a trihydroxy monoene C18 fatty acid with hydroxy groups at C-12 and C-13.

FTIR of the free acid showed absorption of the acid hydroxy group around 2800–3200 $cm^{-1}$ and the alkyl hydroxy groups at 3410 $cm^{-1}$. The FTIR of the methyl ester lacked the absorption for acid hydroxy group at 2800–3200 $cm^{-1}$ but retained the alkyl hydroxy group at 3397 $cm^{-1}$. As expected, the carbonyl at 1710 $cm^{-1}$ for the acid shifted to 1739 $cm^{-1}$ for the ester. Strong CH stretches were seen at 2856 and 2928 $cm^{-1}$. No keto carbonyl was detected. Unsaturation was seen at 3007 $cm^{-1}$. In the absence of a significant absorbance at 970 $cm^{-1}$ (evidence of trans double bonds), the unsaturation seen at 3007 $cm^{-1}$ is presumed to be cis.

The reaction product was also subjected to proton and $^{13}$C NMR analyses. Resonance signals (ppm) and corresponding molecular assignments given in Table I located hydroxy groups at C12, C13, and C17 and identified the bioconversion product as 12,13,17-trihydroxy-9(Z)-octadecenoic acid. The coupling constant of 10.7 Hz at C9,10 confirmed the infrared data that the unsaturation is in cis configuration.

Example 2

In order to develop a production process, the following variables of the bioconversion of linoleic acid to THOA were studied.

Effect of pH

The effect of pH on the production of THOA was studied using 0.1M buffer solutions. Potassium phosphate buffer was used for pH 5.5 to 7.0 and Tris buffer was used for pH 7.5 to 8.5. The production of THOA was found in pH between 6.5 and 8.0 with a peak at 7.0 (Table II).

Effect of Temperature

The effect of temperature on the production of THOA was studied between 15° and 45° C. THOA production was found at temperatures between 25° and 35° C. with a peak at 30° C. (Table III).

Time Course

The reaction was carried out at 30° C. for various periods of time. The amount of the product THOA in the culture media increased with time and reached a maximum after 85 h of reaction (FIG. 1). Further incubation did not reduce THOA content in the medium indicating that strain ALA2 did not metabolize THOA.

TABLE I

Proton and $^{13}$C Nuclear Magnetic Resonance Signals and Molecular Assignments for Bioconversion Product

| Carbon number | $^{13}$C | Proton | Resonance Chemical shifts (ppm)/coupling (Hz) |
|---|---|---|---|
| 1. | 174.4 | — | |
| 2. | 34.1 | 2.29 t | J2,3 = 7.4[a] |
| 3. | 24.9 | 1.60 m | |
| 4. | 29.0 | 1.30 bs | |
| 5. | 29.0 | 1.30 bs | |
| 6. | 29.0 | 1.30 bs | |
| 7. | 29.5 | 1.30 bs | |
| 8. | 27.3 | 2.04 m | J8,9 = 7.0 |
| 9. | 133.8 | 5.55 m | J9,10 = 10.7 |
| 10. | 124.6 | 5.40 m | J10,J11 = 7.2 |
| 11. | 31.7 | 2.29 m | |
| 12[b]. | 73.7 | 3.48 m | |
| 13[b]. | 73.8 | 3.48 m | |
| 14. | 33.5 | 1.48 m | |
| 15. | 21.7 | 1.30 bs | |
| 16. | 39.1 | 1.45 m | |
| 17. | 68.0 | 3.82 m | J17,18 = 6.1 |
| 18. | 23.5 | 1.18 d | |
| $OCH_3$ | 51.5 | 3.65 s | |

[a]Coupling constant J in Hz.
[b]Shift may be interchanged.

TABLE II

Effect of pH on THOA Production

| pH | Product THOA (mg/50 ml) |
|---|---|
| 6.0 | 0 |
| 6.5 | 56 |
| 7.0 | 88 |
| 7.5 | 68 |
| 8.0 | 39 |

TABLE III

Effect of Temperature on THOA Production

| Temperature (C) | Product THOA (mg/50 ml) |
|---|---|
| 20 | 0 |
| 25 | 75 |
| 30 | 90 |
| 35 | 80 |
| 40 | 17 |

I claim:

1. A compound having the formula:

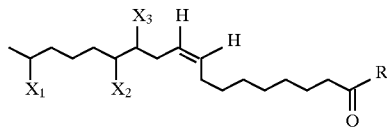

wherein:
R is $-(O)_n-R_1$,
n is 0,1, and
$R_1$ is H, or a hydrocarbon selected from the group consisting of substituted or unsubstituted alkyl, phenyl, or alkyl phenyl hydrocarbons, wherein the alkyl moiety may be branched or straight chain; and
wherein:
$X_1$, $X_2$, and $X_3$ are independently selected from hydroxyl, halogen, or $NR_2R_3$, wherein $R_2$ and $R_3$ are independently selected from the group consisting of hydrogen, substituted or unsubstituted alkyl, phenyl, or alkyl phenyl hydrocarbons, wherein the alkyl moiety may be branched or straight chain.

2. The compound of claim 1 wherein R is hydroxyl and $X_1$, $X_2$, and $X_3$ are hydroxyl.

3. The compound of claim 1 wherein n=1 and $R_1$ is a lower straight chain alkyl having from 1–6 carbons.

4. A method for converting linoleic acid to 12,13,17-trihydroxy-9(Z)-octadecenoic acid comprising cultivating a Clavibacter isolate having all the identifying characteristics of Accession No. NRRL B-21660 on a linoleic acid-containing substrate under conditions suitable for formation of said 12,13,17-trihydroxy-9(Z)-octadecenoic acid.

5. The method of claim 4 wherein said cultivating is conducted at a pH within the range of about 6.5 to 8, and the temperature is within the range of about 25° C. to 40° C.

6. A Clavibacter isolate having all the identifying characteristics of Accession No. NRRL B-21660, including the property of converting linoleic acid to 12,13,17-trihydroxy-9(Z)-octadecenoic acid when said isolate is cultivated on a medium containing linoleic acid at a pH within the range of about 6.5 to 8 and at a temperature within the range of about 25° C. to 40° C.

* * * * *